(12) United States Patent
Dickmann et al.

(10) Patent No.: US 11,534,123 B2
(45) Date of Patent: Dec. 27, 2022

(54) SYSTEM AND METHOD FOR MOVING A GANTRY OF A MEDICAL IMAGING DEVICE

(71) Applicant: Siemens Healthcare GmbH, Erlangen (DE)

(72) Inventors: Christoph Dickmann, Nuremberg (DE); Martin Braeuer, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/410,011

(22) Filed: Aug. 24, 2021

(65) Prior Publication Data

US 2022/0061789 A1 Mar. 3, 2022

(30) Foreign Application Priority Data

Aug. 31, 2020 (DE) ...................... 10 2020 210 968.0

(51) Int. Cl.
*A61B 6/00* (2006.01)
(52) U.S. Cl.
CPC .......... *A61B 6/4447* (2013.01); *A61B 6/4405* (2013.01)
(58) Field of Classification Search
CPC ........ A61B 6/4405; A61B 6/032; A61B 6/035
See application file for complete search history.

(56) References Cited

U.S. PATENT DOCUMENTS

| | | | |
|---|---|---|---|
| 4,645,933 A | 2/1987 | Gambini et al. | |
| 6,959,068 B1 * | 10/2005 | Sommer | A61B 6/04 378/208 |
| 9,161,731 B2 | 10/2015 | Foerner et al. | |
| 9,554,953 B2 | 1/2017 | Dirauf et al. | |
| 9,659,068 B1 | 5/2017 | Mattsson | |
| 2004/0170254 A1 | 9/2004 | Gregerson et al. | |
| 2011/0222667 A1 | 9/2011 | Gregerson et al. | |
| 2014/0079191 A1 | 3/2014 | Aum et al. | |

(Continued)

FOREIGN PATENT DOCUMENTS

| | | |
|---|---|---|
| CN | 108443659 A | 8/2018 |
| CN | 110507345 A | 11/2019 |

(Continued)

OTHER PUBLICATIONS

German Office Action and English translation thereof dated Mar. 26, 2021.

(Continued)

*Primary Examiner* — Dani Fox

(74) *Attorney, Agent, or Firm* — Harness, Dickey & Pierce, P.L.C.

(57) ABSTRACT

A system includes a gantry of a medical imaging device; a linear guide; a carriage system configured to detachably accommodate the gantry and supported in a movable manner via the linear guide parallel to a longitudinal direction relative to a base area; and a drive system configured to move the carriage system parallel to the longitudinal direction relative to the base area while the gantry is accommodated in the carriage system. In at least one embodiment, the gantry includes a chassis configured to move the gantry on the base area in a traveling manner relative to the carriage system while the gantry is detached from the carriage system.

25 Claims, 4 Drawing Sheets

(56) References Cited

U.S. PATENT DOCUMENTS

| | | |
|---|---|---|
| 2017/0325763 A1 | 11/2017 | Hoernig et al. |
| 2018/0184994 A1 | 7/2018 | Keertikumar |
| 2019/0343701 A1 | 11/2019 | Dirauf et al. |
| 2020/0261049 A1 | 8/2020 | Hsieh et al. |

FOREIGN PATENT DOCUMENTS

| | | |
|---|---|---|
| CN | 110559005 A | 12/2019 |
| CN | 110559145 A | 12/2019 |
| CN | 211326357 U | 8/2020 |
| DE | 19908494 A1 | 10/2000 |
| DE | 102012216858 A1 | 3/2014 |
| DE | 102012201529 B4 | 6/2014 |
| DE | 102014213204 A1 | 1/2016 |
| DE | 102016208123 A1 | 9/2017 |
| WO | WO 2004017832 A2 | 3/2004 |
| WO | WO 2018130315 A1 | 7/2018 |

OTHER PUBLICATIONS

German Decision to Grant and English translation thereof dated Apr. 20, 2022.
German Office Action for German Application No. 10 2020 210 968.0 dated Mar. 31, 2021.

\* cited by examiner

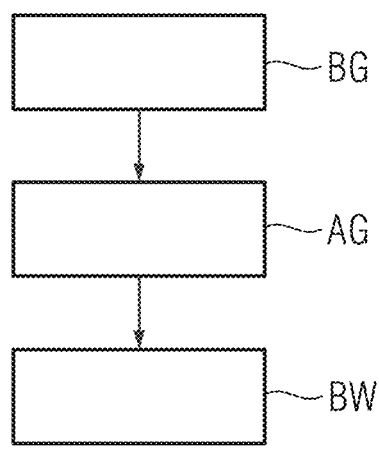
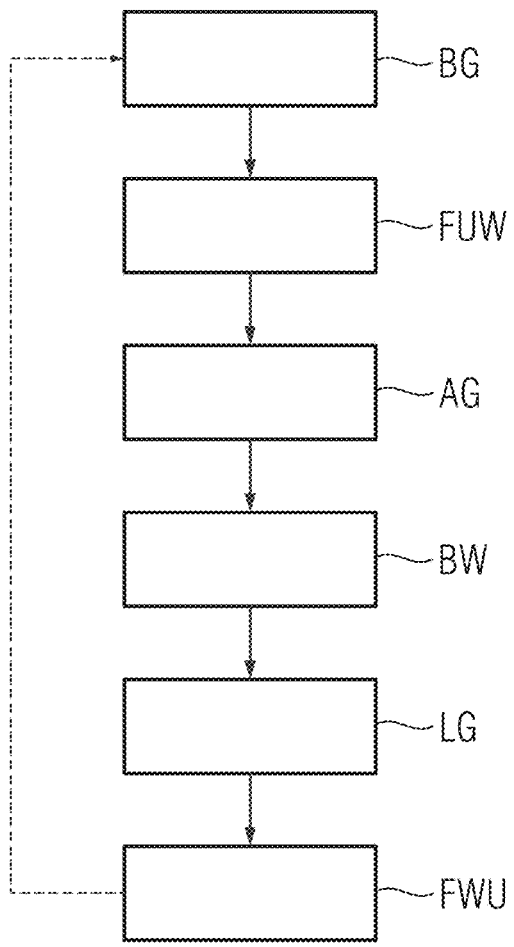

SYSTEM AND METHOD FOR MOVING A GANTRY OF A MEDICAL IMAGING DEVICE

PRIORITY STATEMENT

The present application hereby claims priority under 35 U.S.C. § 119 to German patent application number DE 102020210968.0 filed Aug. 31, 2020, the entire contents of which are hereby incorporated herein by reference.

FIELD

Example embodiments of the invention generally relate to a system and a method for moving a gantry of a medical imaging device.

BACKGROUND

Sectional imaging methods with ring modalities, for example computed tomography devices (CT devices), acquire anatomy and function in patients' bodies quickly and with very good spatial resolution and tissue resolution. This is routinely used in diagnostics around the world, wherein the modality is stationary and the patient moves on a tabletop that is able to travel within the modality.

In minimally invasive therapy, if possible, the patient should not be moved and so the modality should move over the patient. For soft-tissue interventions, for example in tumor therapy, excellent soft-tissue resolution and flexible adjustable scan lengths are required. Large modalities complicate access to the working area on the patient and should therefore only be brought to the patient for the duration of the scan. The rest of the time they should remain in the same room in a remote waiting position or even be available for use in another room for imaging or other interventions.

The flexibility of a moving rail-bound modality is restricted, such as is the case for example with a CT sliding gantry or a ceiling-hung MRI. It is difficult to achieve excellent image quality and high positioning/repositioning accuracy when the modality travels freely on the floor in the room, for example with wheels. Achieving flexible use together with excellent image quality requires complex structures in the room as well as complex structures for the devices.

A rail-supported gantry is, for example, known from U.S. Pat. No. 9,161,731 B2, U.S. Pat. No. 6,959,068 B1, DE 10 2012 201 529 B4 and DE 10 2012 216 858 A1.

A cover for a linear guide and a linear drive is, for example, known from DE 10 2014 213 204 A1.

A mobile gantry on wheels is, for example, known from US 2011/0 222 667 A1, US 2017/0 325 763 A1, U.S. Pat. No. 9,554,953 B, US 2018/0 184 994 A1 and US 2019/0 343 701 A1.

SUMMARY

At least one embodiment of the invention enables improved movement of a gantry of a medical imaging device.

The claims address further advantageous aspects of the invention.

At least one embodiment of the invention relates to a system comprising
 a gantry of a medical imaging device,
 a linear guide,
 a carriage system configured to detachably accommodate the gantry and supported in a movable manner via the linear guide parallel to a longitudinal direction relative to a base area,
 a drive system configured to move the carriage system parallel to the longitudinal direction relative to the base area while the gantry is accommodated in the carriage system, and
 wherein the gantry comprises a chassis configured to move the gantry on the base area in a traveling manner relative to the carriage system while the gantry is detached from the carriage system.

At least one embodiment of the invention further relates to a method for moving a gantry of a medical imaging device, the method including
 moving the gantry via a chassis of the gantry relative to a carriage system configured to detachably accommodate the gantry, wherein the movement takes place on a base area in a traveling manner while the gantry is detached from the carriage system,
 detachably accommodating the gantry in the carriage system, and
 moving the carriage system via a drive system parallel to a longitudinal direction relative to the base area while the gantry is accommodated in the carriage system and the carriage system is supported in a movable manner relative to a base area parallel to the longitudinal direction via a linear guide.

At least one embodiment of the invention further relates to a system, comprising:
 a gantry of a medical imaging device;
 a linear guide;
 a carriage system configured to detachably accommodate the gantry and supported in a movable manner, via the linear guide, parallel to a longitudinal direction relative to a base area; and
 a drive system configured to move the carriage system parallel to the longitudinal direction relative to the base area, while the gantry is accommodated in the carriage system;
 wherein the gantry includes a chassis, configured to move the gantry on the base area in a traveling manner relative to the carriage system, while the gantry is detached from the carriage system.

At least one embodiment of the invention further relates to a method for moving a gantry of a medical imaging device, the method including:
 moving the gantry, via a chassis of the gantry, relative to a carriage system configured to detachably accommodate the gantry, wherein the moving takes place on a base area in a traveling manner while the gantry is detached from the carriage system;
 detachably accommodating the gantry in the carriage system; and
 moving the carriage system, via a drive system, parallel to a longitudinal direction relative to the base area while the gantry is accommodated in the carriage system, the carriage system being supported in a movable manner relative to a base area parallel to the longitudinal direction, via a linear guide.

BRIEF DESCRIPTION OF THE DRAWINGS

The following explains the invention with reference to example embodiments and with reference to the attached figures. The depiction in the figures is schematic, greatly simplified and not necessarily true to scale.

The figures show.

DETAILED DESCRIPTION OF THE EXAMPLE EMBODIMENTS

Figure 1:
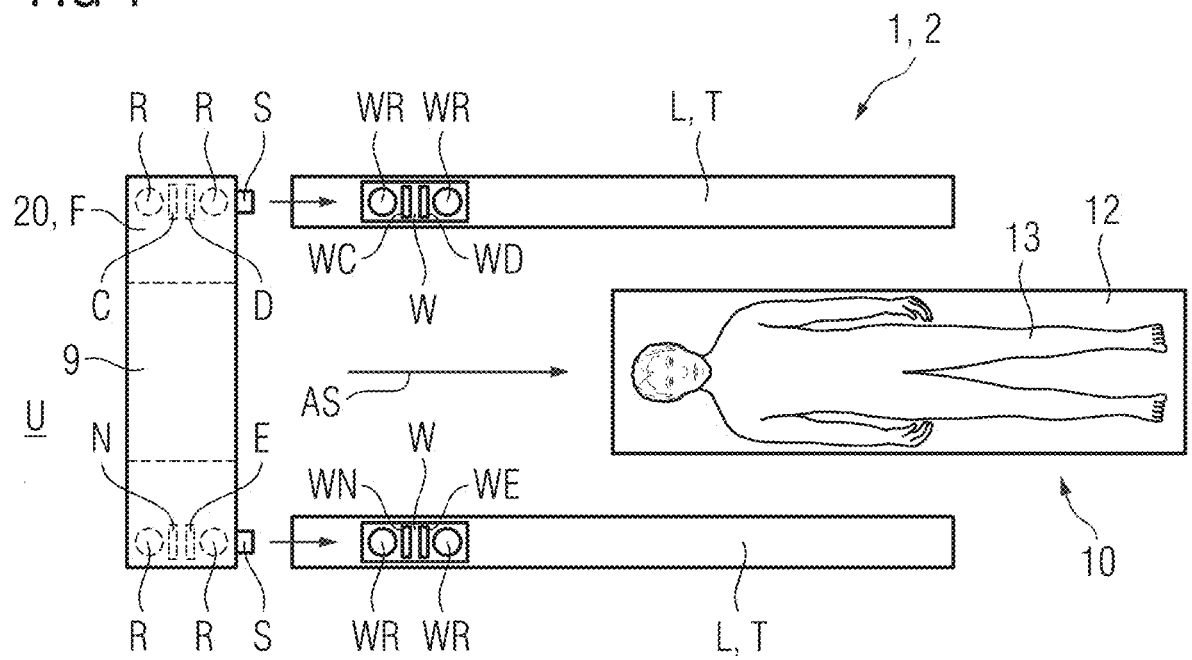
FIG. 1 a system of an embodiment with a gantry of a medical imaging device while the gantry is detached from a carriage system, FIG. 2 the system of an embodiment with the gantry of the medical imaging device while the gantry is accommodated in the carriage system, FIG. 3 the system of an embodiment with the gantry of the medical imaging device while the gantry is accommodated in the carriage system in a side view, FIG. 4 two examination rooms in each case with a linear guide, wherein the gantry of an embodiment can be used in both examination rooms, FIG. 5 a method of an embodiment for moving the gantry of a medical imaging device and FIG. 6 a method of an embodiment for moving the gantry of a medical imaging device according to a further embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a system comprising
a gantry of a medical imaging device,
a linear guide,
a carriage system configured to detachably accommodate the gantry and supported in a movable manner via the linear guide parallel to a longitudinal direction relative to a base area,
a drive system configured to move the carriage system parallel to the longitudinal direction relative to the base area while the gantry is accommodated in the carriage system, and
wherein the gantry comprises a chassis configured to move the gantry on the base area in a traveling manner relative to the carriage system while the gantry is detached from the carriage system.

In particular, the chassis is configured to move the gantry on the base area in a traveling manner relative to the carriage system and relative to the base area while the gantry is detached from the carriage system, in particular while the gantry is detached from the carriage system, from the linear guide and from the drive system.

In particular, it can be provided that the carriage system is also supported in a movable manner via the linear guide antiparallel to the longitudinal direction relative to the base area and that the drive system is also configured to move the carriage system antiparallel to the longitudinal direction relative to the base area while the gantry is accommodated in the carriage system.

In particular, the system can comprise a movement mechanism, wherein the movement mechanism comprises the linear guide, the carriage system and the drive system. The movement mechanism can, for example, be let into a recess of the base area and/or be flush with a surface of the base area.

The carriage system can, for example, comprise a carriage, in particular in the form of a metal plate which is supported via the linear guide.

The carriage system can, for example, comprise a plurality of carriages, wherein, for each carriage of the plurality of carriages, the linear guide comprises a guide rail for supporting this carriage in a moveable manner.

In particular, the linear guide can comprise two mutually parallel guide rails which face each other with respect to a patient support area in which a patient can be supported via the patient support apparatus. In particular, the carriage system can comprise a carriage which is supported in a movable manner via the two mutually parallel guide rails.

In particular, it can be provided that the system comprises a cover for the linear guide and/or the drive system, wherein, at least outside an area directly adjacent to the carriage system, a surface of the cover is flush with a surface of the base area and/or extends in a plane of the surface of the base area.

In particular, it can be provided that the cover is stationary with respect to the longitudinal direction relative to the base area. Such a cover can, for example, be used to cover a moving belt the surface of which is slightly below the surface of the base area.

This can reduce a portion of a surface in the vicinity of the carriage system that moves together with the carriage system.

Furthermore, it can be provided that a leadthrough is embodied in the cover in order to connect the carriage system through the cover to the linear guide and/or to the drive system. In particular, the drive system for the carriage system can comprise at least one linear drive located entirely below the surface of the base area.

In particular, it can be provided that the cover moves locally in the area directly adjacent to the carriage system, for example by raising and/or lowering and/or by an opening perpendicular to the longitudinal direction (such as, for example, in the case of a scissor mechanism) in order to enable the carriage system to move parallel to the longitudinal direction relative to the base area.

This can reduce the risk of stumbling. The movement mechanism can in particular be sealed against the ingress of liquid and/or dust into the movement mechanism. The movement mechanism can in particular be embodied such that, when the gantry is accommodated in the carriage system, oscillation and/or wobbling of the gantry relative to the base area is suppressed, in particular during the movement of the carriage system.

In particular, it can be provided that the system comprises the base area. The linear guide can in particular be stationary relative to the base area and/or anchored in the base area. The base area can, for example, be a floor, in particular a floor of an examination room, and/or comprise a floor plate and/or a base plate. In particular, it can be provided that the surface of the base area is substantially parallel, in particular is parallel, to the horizontal plane.

The gantry is in particular detached from the carriage system when, with the exception of the base area, there is no mechanical connection between the gantry and the carriage system.

One embodiment provides that the carriage system is embodied such that the gantry can travel from the base area onto the carriage system via the chassis and that the gantry can travel from the carriage system onto the base area via the chassis.

One embodiment provides that the chassis and/or the carriage system is configured to secure the gantry against displacement in a horizontal plane relative to the carriage system when the gantry is accommodated in the carriage system.

For example, the gantry can be secured in a form-fitting and/or force-fitting manner against displacement in the horizontal plane relative to the carriage system. For example, the gantry can be secured against displacement in the horizontal plane relative to the carriage system based on a static-friction force acting between the chassis and the carriage system.

For example, the chassis can be detachably connected to the carriage system in the horizontal plane in a form-fitting manner when the gantry is accommodated in the carriage system. In particular, it can be provided that the gantry can be accommodated in the carriage system by fixed anchoring such that, in particular while the imaging data is being acquired, the movement of the carriage system does not cause any change in position of the gantry relative to the carriage system.

One embodiment provides that the chassis comprises a set of wheels and that the chassis is configured to move the gantry on the base area in a traveling manner relative to the carriage system by rolling the wheels of the set of wheels on the base area while the gantry is detached from the carriage system.

The set of wheels can, for example, be a set of omnidirectional wheels, in particular a set of Mecanum wheels. The chassis of the gantry can in particular be omnidirectional and/or embodied to move the gantry relative to the base area.

The carriage system can, for example, comprise areas for accommodating the wheels of the set of wheels. The chassis can, for example, be embodied to brake the wheels of the set of wheels such that the static-friction force acting between the chassis and the carriage system includes a static-friction force acting between the braked wheels of the set of wheels and the carriage system.

One embodiment provides that, for at least one wheel, in particular for each wheel, of the set of wheels, the carriage system comprises a recess for accommodating the corresponding wheel in a form-fitting manner.

Accommodating the wheels of the set of wheels in recesses of the carriage system provided for this purpose in a form-fitting manner enables the gantry to be secured against displacement in a horizontal plane, in particular antiparallel, parallel and/or perpendicular to the longitudinal direction, relative to the carriage system.

In particular, the drive system can be embodied as a linear-drive system. One embodiment provides that the drive system is based on at least one drive for the carriage system selected from the group consisting of a belt drive, a rack-and-pinion drive and a spindle drive.

In particular, the drive system can be embodied in the form of a belt drive or in the form of a plurality of belt drives. In particular, the drive system can be embodied in the form of a rack-and-pinion drive or in the form of a plurality of rack-and-pinion drives. In particular, the drive system can be embodied in the form of a spindle drive or in the form of a plurality of spindle drives. In particular, the drive system can be embodied in the form of a combination of at least two different drives selected from the group.

In particular, the movement mechanism can be embodied in the form of a moving belt or in the form of a plurality of moving belts.

One embodiment provides that the system further comprises a patient support apparatus for supporting a patient, in particular for an examination via the medical imaging device, and that the gantry comprises an acquisition unit configured to acquire imaging data from the patient while the patient is supported on the patient support apparatus, the gantry is accommodated in the carriage system and movement of the carriage system takes place via the drive system parallel to the longitudinal direction relative to the base area.

In particular, the gantry can be moved via the movement mechanism relative to the patient support apparatus in order to acquire the imaging data from the patient while the patient is supported on the patient support apparatus and the gantry is accommodated in the carriage system. Herein, the acquisition unit can, for example, generate and/or receive X-rays.

In particular, the patient support apparatus can comprise a support base and a support plate for supporting the patient, wherein the support plate is arranged on the support base so as to protrude counter to the longitudinal direction.

In particular, it can be provided that the gantry of the medical imaging device comprises a tunnel-shaped opening and/or that by moving the carriage system via the drive system parallel to the longitudinal direction relative to the base area while the gantry is accommodated in the carriage system and the carriage system is supported in a movable manner via a linear guide parallel to the longitudinal direction relative to a base area, a relative movement of the support plate relative to the gantry into the tunnel-shaped opening takes place. Herein, the support plate can rest relative to the base area.

Obstacle detection and/or collision control can also take place during this scan movement. The movement mechanism enables maximum movement precision, for example in the sub-millimeter range, guarantees a defined alignment to the patient support apparatus and clearly marks a movement area for the user.

The patient support apparatus can, for example, be configured for angiography, surgery and/or radiotherapy, in particular in the form of a robot table.

One embodiment provides that the gantry comprises a safety token, wherein the carriage system comprises a verification interface, wherein the safety token and the verification interface are arranged relative to one another such that they can interact with one another at least temporarily in order to identify and/or authenticate the gantry while the gantry is being accommodated in the carriage system and/or while the gantry is accommodated in the carriage system.

The safety token enables the gantry, for example, to log on and/or identify itself individually on the movement mechanism.

It can thus be ensured that control units can reliably identify the gantry and/or the medical imaging device and provide them with the correct actuations, for example in the form of calibration data. The verification interface can, for example, be connected to a control unit via a communication unit in order to transfer data and/or commands, in particular bidirectionally. The control unit can, for example, be arranged centrally in a room provided for this purpose, for example in a special equipment room, so that the control processing does not have to take place in every room in which the gantry is located.

Furthermore, based on the identification and/or authentication of the gantry, the data supplied by the medical imaging device can be used optimally in other devices, in particular in operating units and/or in display units.

The gantry can be operated with and/or without a wired power supply.

One embodiment provides that the gantry comprises an energy store, in particular in the form of a battery and/or an accumulator, wherein the carriage system comprises an energy transfer interface, wherein the gantry and the carriage system can be connected to one another in a detachable manner such that, when the gantry is accommodated in the carriage system, a detachable energy transfer connection for transferring electrical energy, in particular from the energy transfer interface to the energy store, is formed between the energy transfer interface and the energy store.

The gantry can be operated with and/or without a wired data line, for example via WLAN, and/or offers interfaces for travel control, system data and/or positions.

Furthermore, it can be provided that the gantry comprises a data source, wherein the carriage system comprises a data transfer interface, wherein the gantry and the carriage system can be connected to one another in a detachable manner such that, when the gantry is accommodated in the carriage system, a detachable data transfer connection for data transfer, in particular from the data source to the data transfer interface, is formed between the data source and the data transfer interface.

For example, imaging data and/or control data can be transferred via the data transfer connection.

Furthermore, it can be provided that the gantry comprises a cooling system, wherein the carriage system comprises a cooling interface, wherein the gantry and the carriage system can be connected to one another in a detachable manner such that, when the gantry is accommodated in the carriage system, a detachable coolant transfer connection for coolant transfer, in particular for bidirectional coolant transfer, and/or a detachable heat conduction connection for heat conduction, in particular from the cooling system to the cooling interface, is formed between the cooling system and the cooling interface.

At least one embodiment of the invention further relates to a method for moving a gantry of a medical imaging device, the method including moving the gantry via a chassis of the gantry relative to a carriage system configured to detachably accommodate the gantry, wherein the movement takes place on a base area in a traveling manner while the gantry is detached from the carriage system, detachably accommodating the gantry in the carriage system, and moving the carriage system via a drive system parallel to a longitudinal direction relative to the base area while the gantry is accommodated in the carriage system and the carriage system is supported in a movable manner relative to a base area parallel to the longitudinal direction via a linear guide.

One embodiment provides that the method further includes causing the gantry to travel from the base area onto the carriage system via the chassis. One embodiment provides that the method further includes detaching the gantry from the carriage system and/or causing the gantry to travel from the carriage system onto the base area via the chassis.

For example, after a transfer, the gantry can travel onto the carriage system via the chassis. Herein, position information relating to the positioning of the gantry relative to the carriage system, in particular positioning accuracy, can be acquired via a position sensor. Corresponding feedback can be output to the user, for example with a display as to whether the positioning has taken place within a prespecified tolerance range.

When the acquisition of the imaging data is complete, the gantry can, for example, travel again from the carriage system onto the base area and switch to transfer mode.

One embodiment provides that the gantry is secured via the chassis and/or the carriage system against displacement in a horizontal plane relative to the carriage system when the gantry is accommodated in the carriage system.

One embodiment provides that imaging data from a patient is acquired via an acquisition unit of the gantry, in particular based on a scan protocol of the medical imaging device, while the patient is supported on a patient support apparatus and the movement of the carriage system takes place.

The scan protocol can in particular be set patient-specifically and/or examination-specifically. The movement of the carriage system can in particular take place based on control data generated based on the scan protocol of the medical imaging device.

In particular, communication can be provided between the gantry and the patient support apparatus in order, for example, to be able to adjust a table height or a movement of the patient support plate specific to the gantry or an optimal scan.

One embodiment provides that the gantry comprises a safety token, wherein the carriage system comprises a verification interface, wherein the gantry is identified and/or authenticated in that the safety token and the verification interface interact at least temporarily while the gantry is being accommodated in the carriage system and/or while the gantry is accommodated in the carriage system.

One embodiment provides that a detachable energy transfer connection for transferring electrical energy, in particular from the energy transfer interface to the energy store, is formed between an energy store of the gantry and an energy transfer interface of the carriage system, wherein the electrical energy is transferred from the energy transfer interface to the energy store via the detachable energy transfer connection.

Furthermore, it can be provided that a detachable data transfer connection for data transfer, in particular from the data source to the data transfer interface, is formed between a data source of the gantry and a data transfer interface of the carriage system, wherein data is transferred via the detachable data transfer connection from the data source to the data transfer interface. For example, imaging data and/or control data can be transferred via the data transfer connection.

Furthermore, it can be provided that a detachable coolant transfer connection for coolant transfer, in particular for bidirectional coolant transfer, and/or a detachable heat conduction connection for heat conduction, in particular from the cooling system to the cooling interface, is formed between a cooling system of the gantry and a cooling interface of the carriage system, wherein coolant is transferred via the detachable coolant transfer connection, in particular bidirectionally, and/or wherein heat is transferred, in particular from the cooling system to the cooling interface, via the detachable heat conduction connection.

The gantry can move along a defined path or in a manner freely controlled by the user between two or more sites of usage, for example examination rooms. Herein, there is a safety system that detects obstacles and the path of travel to the extent that collisions are avoided in good time. Herein, the gantry can be moved freely or with tools on paths that can be stored exactly as they are in the system. These routes and positions can later be selected again by the user and used as a transfer.

The two travel mechanisms enable the gantry to be used in one single room or in a plurality of rooms. A corresponding movement mechanism should be installed in each room. If the gantry is to be used exclusively in one room, the gantry can be connected directly to the carriage system without wheels.

The system not only allows the use of a modality that can be brought to a plurality of different locations where the stationary movement mechanisms are located in each case; it also allows the use of a movement mechanism, for example in a treatment room with a plurality of different modalities. Therefore, for example, it is optionally possible to use a first CT modality or a second CT modality for scanning and also a completely different modality such as, for example, an MR scanner, in one examination room.

Thus, the optimal modality for the specific treatment can be used in each case in a specific treatment room without all modalities having to be in the same room at the same time.

The system can further be used in connection with at least one other movable system, for example in the form of Angio-CT or a LINAC-CT combination.

The system can be operated in different modes that a user can select and actuate by way of specific functions.

According to a waiting mode it is, for example, provided that, starting from the transfer mode or from the scan mode, the gantry is parked at a storable position in which in particular no scan can take place and/or energy and/or cooling can be saved.

According to a park mode it is, for example, provided that the gantry can be positioned and parked in defined areas in order to stand there unused for a longer period of time. There, for example, as in the waiting position, energy can be saved, the energy store can be charged via a corresponding detachable energy transfer connection, the system can be maintained (for example remotely) via a corresponding detachable data transfer connection, the system can be switched off, etc. Herein, the gantry can be parked in a space-saving manner, for example in a treatment room, in a separate room or in a niche.

According to a cleaning mode, cleaning of the travel systems can be performed manually by the user and/or at least partially automated. This can prevent infectious material being spread on or in the floor. According to a service mode, it is, for example, provided that the system requests and/or is provided with maintenance, configuration and/or servicing functions, which can, in particular, be performed on site or remotely. Herein, the gantry can move to a limited extent and/or trigger radiation on a test basis.

A particular advantage arises in the case of gantry defects. In this case, the gantry does not need to be repaired in the treatment room but can be transferred to another position where the repair can take place independently of the hospital's medical services. If a large hospital is suitably equipped, it is also simple to bring a replacement device into the corresponding room.

In particular, the movement mechanism can enable very precise imaging with diagnostic image quality. Thus, even a gantry weighing more than 1.5 metric tons can be moved safely and precisely for image acquisition.

The movement mechanism used for the scan is permanently installed in the floor and embodied as separate from the gantry. Thus, the gantry can be embodied with a lower mass and as more compact and less complex than a gantry that comprises a transfer travel system and a scan travel system.

Further, the movement mechanism used for the scan can be embodied as more complex and heavier in order to improve precision during the scan without this impairing the mobility of the gantry.

The described solution also makes it possible to dispense with complex mechanics in the gantry that may be required in some circumstances for a scan movement effected by the rolling of wheels on a base area, for example for height compensation and/or to regulate straight-ahead travel during the scan.

In particular, it can be provided that the system comprises the medical imaging device.

The medical imaging device can, for example, be selected from the imaging modality group consisting of an X-ray device, a C-arm X-ray device, a computed tomography device (CT device), a molecular imaging device (MI device), a single-photon emission computed tomography device (SPECT device), a positron emission tomography device (PET device), a magnetic resonance tomography device (MR device) and combinations thereof, in particular a PET-CT device and a PET-MR device. The medical imaging device can further comprise a combination of an imaging modality selected, for example, from the imaging modality group and an irradiation modality. Herein, the irradiation modality can, for example, comprise an irradiation unit for therapeutic irradiation.

The gantry of the medical imaging device typically comprises a support structure on which in particular components of the acquisition unit, in particular the radiation source and/or the radiation detector, are arranged.

The support structure of the gantry typically has such high rigidity and strength that the components of the acquisition unit can be arranged both relative to one another and relative to an area to be imaged in a geometry that is sufficiently defined for imaging.

In a computed tomography device, the gantry typically comprises a support frame and a rotor supported rotatably relative to the support frame, wherein the radiation source and the radiation detector are arranged on the rotor. Optionally, the gantry can comprise a tilting frame supported tiltably relative to the support frame, wherein the rotor is arranged on the tilting frame.

The use of the indefinite article "a" or "an" does not preclude the possibility that the feature in question may also be present on a multiple basis. The use of the expression "comprises" does not preclude the possibility that the terms linked by way of the expression "comprises" may be identical. The use of the expression "unit" does not preclude the possibility that the subject matter to which the expression "unit" relates can comprise a plurality of components that are spatially separated from one another.

FIG. 1 shows a system with a gantry of a medical imaging device while the gantry is detached from a carriage system.

The system 1 further comprises a linear guide L, a carriage system W and a drive system T.

The carriage system W is configured to accommodate the gantry 20 in a detachable manner and is supported via the linear guide L so as to be movable relative to a base area U parallel and antiparallel to the longitudinal direction AS. The drive system T is configured to move the carriage system W parallel to the longitudinal direction AS relative to the base area U while the gantry 20 is accommodated in the carriage system W. The drive system T is further configured to move the carriage system W antiparallel to the longitudinal direction AS relative to the base area U while the gantry 20 is accommodated in the carriage system W.

The gantry 20 comprises a chassis F configured to move the gantry 20 on the base area U in a traveling manner relative to the carriage system W while the gantry 20 is detached from the carriage system W. The carriage system W is embodied such that the gantry 20 can travel from the base area U onto the carriage system W via the chassis F and that the gantry 20 can travel from the carriage system W onto the base area U via the chassis F. The chassis F and the carriage system W are configured to secure the gantry 20 against displacement in a horizontal plane H relative to the carriage system W when the gantry 20 is accommodated in the carriage system W.

The chassis F comprises a set of wheels, wherein the chassis F is configured to move the gantry 20 on the base area U in a traveling manner relative to the carriage system W by rolling the wheels of the set of wheels on the base area U while the gantry 20 is detached from the carriage system W. For each wheel R of the set of wheels, the carriage system W comprises a recess WR accommodating the corresponding wheel R in a form-fitting manner.

A travel system for the transfer includes the chassis F with the wheels R and the sensors S, which can, for example, be embodied for orientation in the room and for collision avoidance. The chassis F has interfaces for system control and for energy exchange and is integrated in the safety system of the medical imaging device 2. The wheels R are in each case attached to the outer end of a base area of the gantry 20 so that they provide the greatest possible stability. They are attached in such a way that they require a maximum of two accommodating areas of the carriage system W in the longitudinal direction AS.

Two moving belts aligned in the longitudinal direction AS are provided and extend as far as next to the foot of the patient support apparatus 10. The carriage system W comprises two separate carriages, which in each case comprise areas for accommodating the wheels. Alternatively, the carriage system W can comprise a carriage that is supported in a movable manner via the two moving belts. The drive system T in each case comprises a belt drive for each of the two moving belts.

The linear guide L, the carriage system W and the drive system T enable the gantry 20 to move uniformly and synchronously at speeds that also permit rapid image acquisition, for example for a pitch of 1.7, which can mean a travel speed of up to 200 mm/s.

Figure 2:
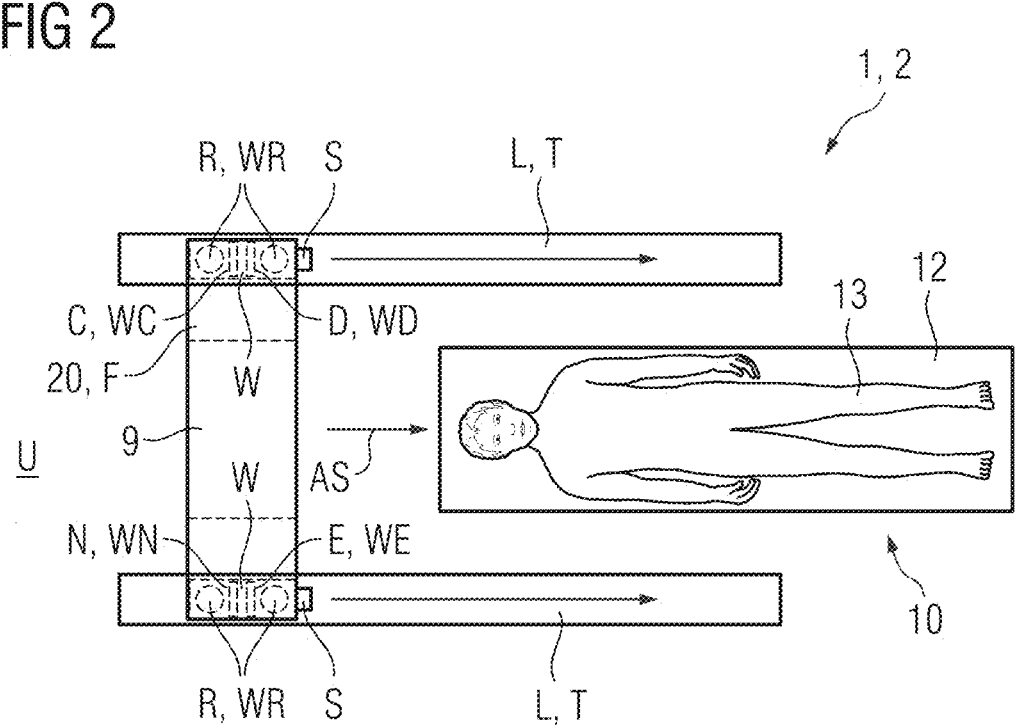

FIG. 2 shows the system with the gantry of the medical imaging device while the gantry is accommodated in the carriage system.

The gantry 20 comprises a safety token N, wherein the carriage system W comprises a verification interface WN, wherein the safety token N and the verification interface WN are arranged relative to one another such that they can interact with one another at least temporarily in order to identify and/or authenticate the gantry 20 while the gantry 20 is being accommodated in the carriage system W and/or while the gantry 20 is accommodated in the carriage system W.

The gantry 20 comprises an energy store E, wherein the carriage system W comprises an energy transfer interface WE, wherein, when the gantry 20 is accommodated in the carriage system W, the gantry 20 and the carriage system W can be connected to one another in a detachable manner such that a detachable energy transfer connection for transferring electrical energy, in particular from the energy transfer interface to the energy store, is formed between the energy transfer interface WE and the energy store E.

The gantry 20 comprises a data source D, wherein the carriage system W comprises a data transfer interface WD, wherein the gantry 20 and the carriage system W can be connected to one another in a detachable manner such that, when the gantry 20 is accommodated in the carriage system W, a detachable data transfer connection for data transfer, in particular from the data source to the data transfer interface, is formed between the data source D and the data transfer interface WD.

The gantry 20 comprises a cooling system C, wherein the carriage system W comprises a cooling interface WC, wherein the gantry 20 and the carriage system W can be connected to one another in a detachable manner such that, when the gantry 20 is accommodated in the carriage system W, a detachable coolant transfer connection for coolant transfer and/or a detachable heat conduction connection for heat conduction is formed between the cooling system C and the cooling interface WC.

Figure 3:
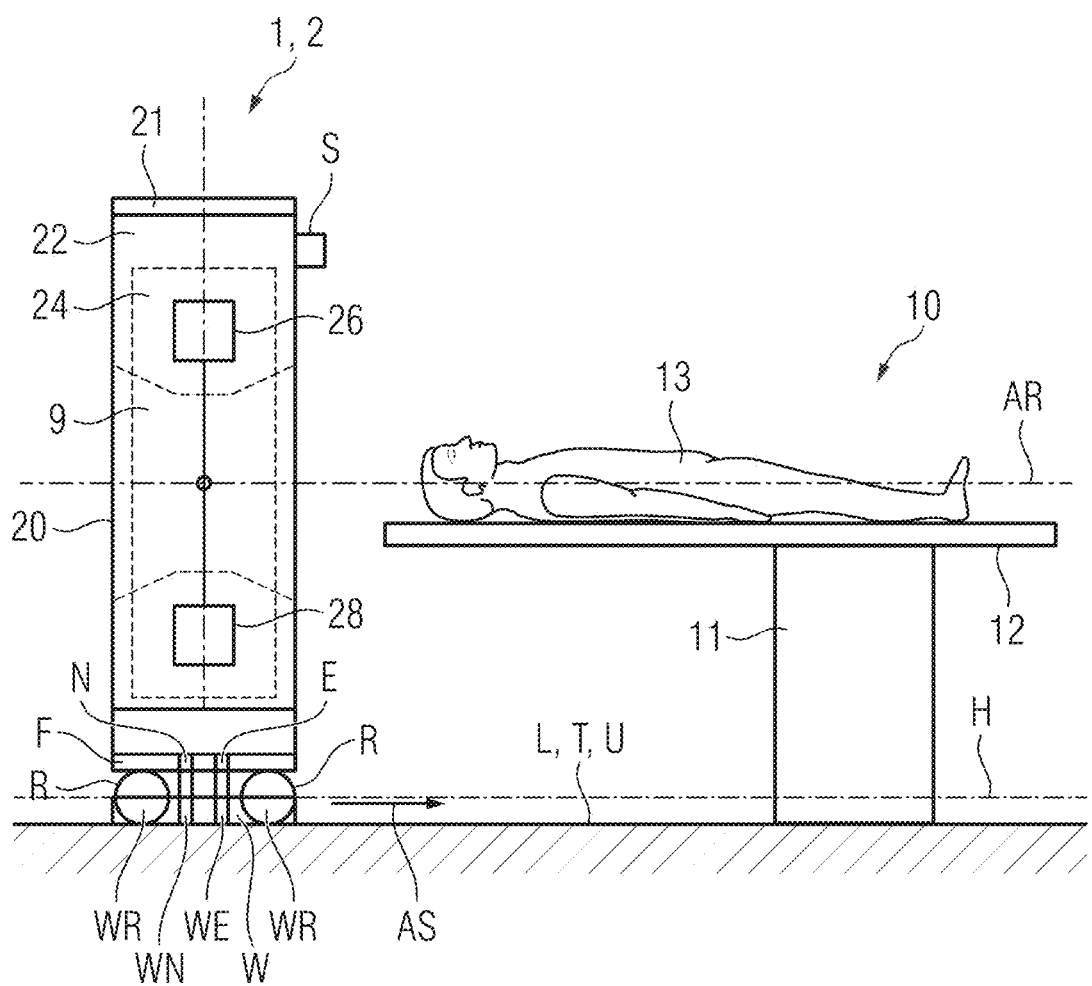

FIG. 3 shows the system with the gantry of the medical imaging device while the gantry is accommodated in the carriage system in a side view.

The system 1 further comprises a patient support apparatus 10 for supporting a patient 13 for an examination via the medical imaging device 2. In the example depicted, the medical imaging device 2 is a computed tomography device.

The gantry 20 comprises a support frame 21 and a tilting frame 22 supported tiltably on the support frame 21 relative to the support frame 21 about a horizontal tilting axis. The gantry further comprises the rotor 24 arranged on the tilting frame 22 so as to be rotatable about an axis of rotation relative to the tilting frame 22 via a rotary supporting apparatus. The patient 13 can be introduced into the tunnel-shaped opening 9. An area of the patient 13 can be positioned in the tunnel-shaped opening 9 such that the radiation 27 from the X-ray source 26 can reach the area to be imaged and, after interaction with the area to be imaged, can reach the radiation detector 28.

The gantry 20 comprises an acquisition unit in the form of the X-ray source 26 and the X-ray detector 28 that interacts with the X-ray source which is configured to acquire imaging data from the patient 13 while the patient 13 is supported on the patient support apparatus 10, the gantry 20 is accommodated in the carriage system W and movement of the carriage system W via the drive system T takes place parallel to the longitudinal direction AS relative to the base area 10.

The patient support apparatus 10 comprises a support base 11 and a support plate 12 for supporting the patient 13, wherein the support plate 12 is arranged on the support base 11 so as to protrude counter to the longitudinal direction AS.

The gantry 20 of the medical imaging device 2 comprises a tunnel-shaped opening 9. By moving BW the carriage system W via the drive system T parallel to the longitudinal direction AS relative to the base area U while the gantry 20 is accommodated in the carriage system W and the carriage system W is supported in a movable manner via a linear guide L parallel to the longitudinal direction AS relative to a base area U, a relative movement of the support plate 12 relative to the gantry 20 into the tunnel-shaped opening 9 takes place.

The longitudinal direction AS is parallel to the system axis AR of the medical imaging device 2 and parallel to a longitudinal direction of the patient 13. When the tilting frame 22 is not tilted relative to the support frame 21, the axis of rotation is parallel to the system axis AR.

Figure 4:
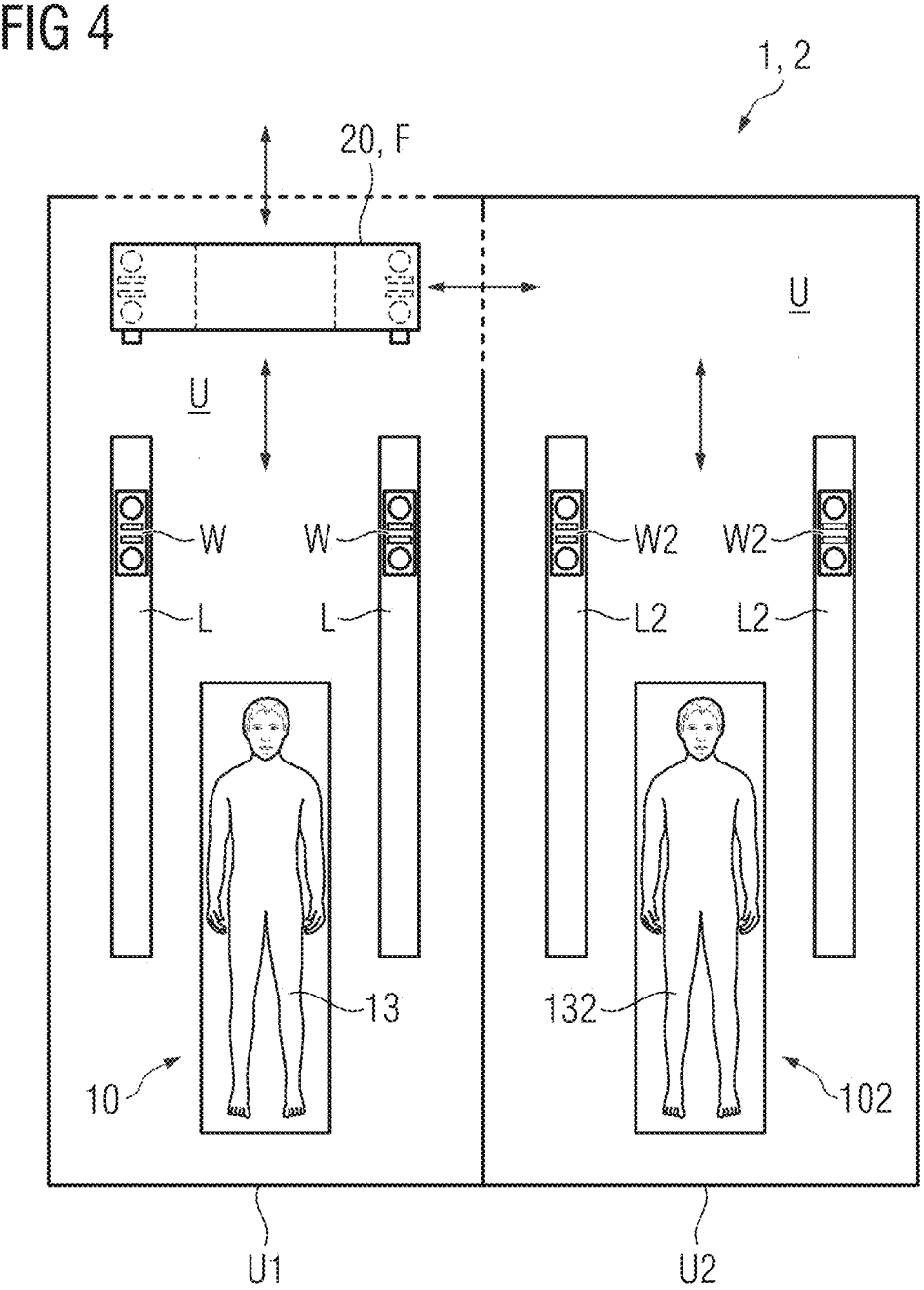

FIG. 4 shows two examination rooms with a linear guide in each case, wherein the gantry can be used in both examination rooms.

The gantry 20 is transferred between the examination rooms U1 and U2 via the chassis F. For the image acquisition, the gantry 20 is in each case accommodated in the corresponding carriage system W or W2. The gantry 20 can also leave the examination rooms U1 and U2 via the chassis F and travel to a more distant location.

FIG. 5 shows a method for moving the gantry of a medical imaging device, the method including moving BG the gantry 20 via a chassis F of the gantry 20 relative to a carriage system W configured to detachably accommodate the gantry 20, wherein the movement takes place on a base area U in a traveling manner while the gantry 20 is detached from the carriage system W, detachably accommodating AG the gantry 20 in the carriage system W, and moving BW the carriage system W via a drive system T parallel to a longitudinal direction AS relative to the base area U while the gantry 20 is accommodated in the carriage system W and the carriage system W is supported in a moveable manner relative to a base area U via a linear guide L parallel to the longitudinal direction AS.

FIG. 6 shows a method for moving the gantry of a medical imaging device according to a further embodiment further including causing the gantry 20 to travel FUW from the base area U onto the carriage system W via the chassis F, detaching LG the gantry 20 from the carriage system W, causing the gantry 20 to travel FWU from the carriage system W onto the base area U via the chassis F.

When the gantry 20 is detached LG from the carriage system W the gantry 20 can, for example, be logged off from the movement mechanism and/or a detachable connection between the gantry 20 and the carriage system W can be detached, in particular the detachable energy transfer connection, the detachable data transfer connection, the detachable coolant transfer connection and/or the detachable heat conduction connection, can be detached. The detachable connection can in particular be detached automatically and/or without manual intervention.

The dashed arrow indicates that, after the gantry 20 has traveled FWU from the carriage system W onto the base area U via the chassis F, the movement BG of the gantry 20 can take place again.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system, comprising:
   a gantry of a medical imaging device;
   a linear guide;
   a carriage system configured to detachably accommodate the gantry and supported in a movable manner, via the linear guide, parallel to a longitudinal direction relative to a base area; and
   a drive system configured to move the carriage system parallel to the longitudinal direction relative to the base area, while the gantry is accommodated in the carriage system;
   wherein the gantry includes a chassis, configured to move the gantry on the base area in a traveling manner relative to the carriage system, while the gantry is detached from the carriage system.

2. The system of claim 1, wherein the carriage system is embodied to enable the gantry to travel from the base area onto the carriage system via the chassis and to enable the gantry to travel from the carriage system onto the base area via the chassis.

3. The system of claim 2, wherein at least one of the chassis and the carriage system is configured to secure the gantry against displacement in a horizontal plane relative to the carriage system, when the gantry is accommodated in the carriage system.

4. The system of claim 2,
   wherein the chassis includes a set of wheels, and
   wherein the chassis is configured to move the gantry on the base area in a traveling manner relative to the carriage system by rolling the wheels of the set of wheels on the base area while the gantry is detached from the carriage system.

5. The system of claim 4, wherein, for at least one wheel of the set of wheels, the carriage system includes a recess to accommodate the at least one wheel in a form-fitting manner.

6. The system of claim 2, wherein the drive system is based on at least one drive for the carriage system selected from the group consisting of a belt drive, a rack-and-pinion drive and a spindle drive.

7. The system of claim 2, further comprising:
   a patient support apparatus to support a patient,
   wherein the gantry includes at least one processor to acquire imaging data from the patient while the patient is supported on the patient support apparatus, the gantry being accommodated in the carriage system, and movement of the carriage system via the drive system taking place parallel to the longitudinal direction relative to the base area.

8. The system of claim 2,
   wherein the gantry includes a safety token,
   wherein the carriage system includes a verification interface, and
   wherein the safety token and the verification interface are arranged relative to one another to interact with one another at least temporarily in order to at least one of identify and authenticate the gantry at least one of while the gantry is being accommodated in the carriage system and while the gantry is accommodated in the carriage system.

9. The system of claim 1, wherein at least one of the chassis and the carriage system is configured to secure the gantry against displacement in a horizontal plane relative to the carriage system, when the gantry is accommodated in the carriage system.

10. The system of claim 1,
    wherein the chassis includes a set of wheels, and
    wherein the chassis is configured to move the gantry on the base area in a traveling manner relative to the carriage system by rolling the wheels of the set of wheels on the base area while the gantry is detached from the carriage system.

11. The system of claim 10, wherein, for at least one wheel of the set of wheels, the carriage system includes a recess to accommodate the at least one wheel in a form-fitting manner.

12. The system of claim 1, wherein the drive system is based on at least one drive for the carriage system selected from the group consisting of a belt drive, a rack-and-pinion drive and a spindle drive.

13. The system of claim 1, further comprising:
    a patient support apparatus to support a patient,
    wherein the gantry includes an acquisition unit configured to acquire imaging data from the patient while the patient is supported on the patient support apparatus, the gantry being accommodated in the carriage system, and movement of the carriage system via the drive system taking place parallel to the longitudinal direction relative to the base area.

14. The system of claim 1,
    wherein the gantry includes a safety token,
    wherein the carriage system includes a verification interface, and
    wherein the safety token and the verification interface are arranged relative to one another to interact with one another at least temporarily in order to at least one of identify and authenticate the gantry at least one of while the gantry is being accommodated in the carriage system and while the gantry is accommodated in the carriage system.

15. The system of claim 1,
    wherein the gantry includes an energy store,
    wherein the carriage system includes an energy transfer interface, and
    wherein, when the gantry is accommodated in the carriage system, the gantry and the carriage system are connectable to in a detachable manner such that a detachable energy transfer connection for transferring electrical energy is formed between the energy transfer interface and the energy store.

16. A method for moving a gantry of a medical imaging device, the method including:
    moving the gantry, via a chassis of the gantry, relative to a carriage system configured to detachably accommodate the gantry, wherein the moving takes place on a base area in a traveling manner while the gantry is detached from the carriage system;
    detachably accommodating the gantry in the carriage system; and
    moving the carriage system, via a drive system, parallel to a longitudinal direction relative to the base area while the gantry is accommodated in the carriage system, the carriage system being supported in a movable manner relative to a base area parallel to the longitudinal direction, via a linear guide.

17. The method of claim 16, further comprising
    causing the gantry to travel from the base area onto the carriage system via the chassis;
    detaching the gantry from the carriage system;
    causing the gantry to travel from the carriage system onto the base area via the chassis.

18. The method of claim 17, wherein the gantry is secured against displacement in a horizontal plane relative to the carriage system via at least one of the chassis and the carriage system when the gantry is accommodated in the carriage system.

19. The method of claim 17, wherein imaging data from a patient is acquired via an acquisition unit of the gantry while the patient is supported on a patient support apparatus and the movement of the carriage system takes place.

20. The method of claim 17,
wherein the gantry includes a safety token,
wherein the carriage system includes a verification interface, and
wherein the gantry is at least one of identified and authenticated, in that the safety token and the verification interface interact at least temporarily at least one of while the gantry is being accommodated in the carriage system and while the gantry is accommodated in the carriage system.

21. The method of claim 17,
wherein a detachable energy transfer connection for transferring electrical energy is formed between an energy store of the gantry and an energy transfer interface of the carriage system, and
wherein the electrical energy is transferred from the energy transfer interface to the energy store via the detachable energy transfer connection.

22. The method of claim 16, wherein the gantry is secured against displacement in a horizontal plane relative to the carriage system via at least one of the chassis and the carriage system when the gantry is accommodated in the carriage system.

23. The method of claim 16, wherein imaging data from a patient is acquired via an acquisition unit of the gantry while the patient is supported on a patient support apparatus and the movement of the carriage system takes place.

24. The method of claim 16,
wherein the gantry includes a safety token,
wherein the carriage system includes a verification interface, and
wherein the gantry is at least one of identified and authenticated, in that the safety token and the verification interface interact at least temporarily at least one of while the gantry is being accommodated in the carriage system and while the gantry is accommodated in the carriage system.

25. The method of claim 16,
wherein a detachable energy transfer connection for transferring electrical energy is formed between an energy store of the gantry and an energy transfer interface of the carriage system, and
wherein the electrical energy is transferred from the energy transfer interface to the energy store via the detachable energy transfer connection.

* * * * *